(12) United States Patent
Kim

(10) Patent No.: US 10,445,970 B2
(45) Date of Patent: Oct. 15, 2019

(54) MEDICINE-DISPENSING APPARATUS

(71) Applicant: JVM CO., LTD., Daegu (KR)

(72) Inventor: Jun-Ho Kim, Daegu (KR)

(73) Assignee: JVM CO., LTD., Daegu (KR)

( * ) Notice: Subject to any disclaimer, the term of this patent is extended or adjusted under 35 U.S.C. 154(b) by 11 days.

(21) Appl. No.: 15/718,361

(22) Filed: Sep. 28, 2017

(65) Prior Publication Data

US 2018/0089924 A1  Mar. 29, 2018

Related U.S. Application Data

(63) Continuation-in-part of application No. 15/676,553, filed on Aug. 14, 2017.

(30) Foreign Application Priority Data

Sep. 23, 2016  (KR) .................. 10-2016-0121875

(51) Int. Cl.
| | |
|---|---|
| *G07F 11/10* | (2006.01) |
| *G07F 11/26* | (2006.01) |
| *G07F 11/58* | (2006.01) |
| *A61J 7/00* | (2006.01) |
| *G06F 19/00* | (2018.01) |
| *G07F 17/00* | (2006.01) |
| *G16H 20/13* | (2018.01) |

(52) U.S. Cl.
CPC ............. *G07F 11/10* (2013.01); *A61J 7/0084* (2013.01); *G06F 19/3462* (2013.01); *G07F 11/26* (2013.01); *G07F 11/58* (2013.01); *G07F 17/0092* (2013.01); *G16H 20/13* (2018.01)

(58) Field of Classification Search
CPC ........ B65D 83/02; B65G 47/06; B23Q 41/02; G07F 11/10; G07F 11/26; G07F 11/58; G07F 17/0092; A16H 20/13; G15H 20/13
USPC ........ 221/1, 174, 201, 257, 9; 414/748, 900, 414/745
See application file for complete search history.

(56) References Cited

U.S. PATENT DOCUMENTS

| | | | | |
|---|---|---|---|---|
| 488,084 | A * | 12/1892 | Miner .................. | B65G 59/067 221/238 |
| 541,853 | A * | 7/1895 | Hart ....................... | A24F 15/10 221/142 |
| 1,159,195 | A * | 11/1915 | Eden, Jr. .............. | B65G 59/067 221/238 |
| 1,457,050 | A * | 5/1923 | Abbaticchio ........... | A24F 27/22 221/254 |

(Continued)

*Primary Examiner* — Rakesh Kumar
(74) *Attorney, Agent, or Firm* — Novick, Kim & Lee, PLLC; Jae Youn Kim

(57) ABSTRACT

A medicine-dispensing apparatus is disclosed. The apparatus includes a medicine storage unit for separately containing a plurality of medicines, and a medicine transfer unit for receiving the plurality of medicines moved from the medicine storage unit in a first direction and transferring the plurality of medicines in a second direction, wherein the medicine transfer unit includes a frame unit on which the plurality of medicines are placed and a medicine-pushing unit movably disposed in the frame unit so as to transfer the plurality of medicines placed on the frame unit in the second direction, and wherein the medicine-pushing unit is able to be projected from and retracted into an internal space of the frame unit so as to move the plurality of medicines placed on the frame unit in the second direction.

11 Claims, 15 Drawing Sheets

(56) References Cited

U.S. PATENT DOCUMENTS

| | | | | |
|---|---|---|---|---|
| 1,498,476 A * | 6/1924 | Nadwocki | A24F 15/04 | 221/248 |
| 1,696,787 A * | 12/1928 | Zelkowitz | A24F 15/04 | 221/254 |
| 2,346,863 A * | 4/1944 | Pacione | A24F 15/04 | 221/131 |
| 2,407,638 A * | 9/1946 | Gettig | B65G 47/1478 | 221/236 |
| 2,541,945 A * | 2/1951 | Smith | A24F 15/04 | 221/254 |
| 3,232,449 A * | 2/1966 | Shen | B21B 39/002 | 414/746.1 |
| 3,703,232 A * | 11/1972 | Zbiegien | B65B 35/56 | 198/383 |
| 3,743,135 A * | 7/1973 | Brumley | B65D 88/64 | 221/205 |
| 3,746,212 A * | 7/1973 | Anderheggen | B65G 47/1407 | 198/540 |
| 3,777,932 A * | 12/1973 | Matsui | B65G 65/42 | 221/204 |
| 4,101,284 A * | 7/1978 | Difiglio | G01N 33/54366 | 221/264 |
| 4,362,460 A * | 12/1982 | Peddinghaus | B65G 47/1478 | 198/443 |
| 4,388,039 A * | 6/1983 | Schwarze | B21D 43/006 | 198/543 |
| 4,548,537 A * | 10/1985 | Kubotera | B21F 23/007 | 221/210 |
| 4,573,860 A * | 3/1986 | Peddinghaus | B65G 47/1478 | 198/443 |
| 4,574,942 A * | 3/1986 | Gordon | B65G 25/08 | 198/463.5 |
| 4,805,376 A * | 2/1989 | Oberdorf | B65B 19/10 | 198/468.1 |
| 4,809,882 A * | 3/1989 | Neu | B65G 47/1478 | 221/238 |
| 4,946,024 A * | 8/1990 | Forsberg | B65G 47/82 | 198/429 |
| 4,982,891 A * | 1/1991 | Kimura | B21D 11/10 | 228/155 |
| 5,067,631 A * | 11/1991 | Baba | B65G 47/1478 | 221/254 |
| 5,082,419 A * | 1/1992 | Kollross | A22C 15/001 | 198/774.1 |
| 5,238,353 A * | 8/1993 | Kollross | A22C 15/001 | 198/803.14 |
| 5,568,881 A * | 10/1996 | Chi | B01L 9/543 | 221/172 |
| 5,592,898 A * | 1/1997 | Korpi | E01F 9/688 | 116/202 |
| 5,647,472 A * | 7/1997 | Fierkens | B65G 47/1471 | 198/443 |
| 5,899,357 A * | 5/1999 | Yuyama | B65B 35/08 | 221/171 |
| 6,039,209 A * | 3/2000 | Yuyama | B65G 47/1478 | 221/171 |
| 6,138,868 A * | 10/2000 | Yuyama | G07F 11/44 | 221/156 |
| 6,189,728 B1 * | 2/2001 | Yuyama | B65G 47/1471 | 221/17 |
| 6,505,756 B1 * | 1/2003 | Walldorf | B65G 47/1471 | 221/241 |
| 6,640,428 B2 * | 11/2003 | Barber | A61M 5/32 | 221/254 |
| 6,860,694 B2 * | 3/2005 | Slettedal | E21B 19/155 | 414/22.51 |
| 7,089,654 B2 * | 8/2006 | Chiba | B23P 19/001 | 221/236 |
| 7,299,943 B2 * | 11/2007 | Itoh | B01L 9/543 | 221/242 |
| 7,504,067 B2 * | 3/2009 | Itoh | B65G 47/1478 | 156/538 |
| 7,824,250 B2 * | 11/2010 | Topfer | B65G 59/062 | 452/51 |
| 8,662,606 B2 * | 3/2014 | Santmyer | G07F 11/62 | 312/319.7 |
| 9,757,309 B2 * | 9/2017 | Okutsu | A61J 7/0076 | |
| 2011/0272425 A1 * | 11/2011 | Wiemer | A22C 15/001 | 221/1 |
| 2018/0089924 A1 * | 3/2018 | Kim | G07F 11/10 | |

* cited by examiner

MEDICINE-DISPENSING APPARATUS

CROSS-REFERENCE TO PRIOR APPLICATION

This is a continuation-in-part application of U.S. Ser. No. 15/676,553 filed Aug. 14, 2017, and the disclosure of which is entirely incorporated herein.

BACKGROUND OF THE INVENTION

Field of the Invention

The present invention relates to a medicine-dispensing apparatus, and more particularly to a medicine-dispensing apparatus capable of dispensing medicines with improved efficiency.

Description of the Related Art

Generally, medicines prescribed to patients may include medicines packaged in various kinds and shapes of single-dosage forms, and an envelope containing single doses of respective medicines is transferred to the patient.

Specifically, in the prescription of medication, various kinds and shapes of medicines prescribed to a patient are collected into an envelope from respective medicine containers, and the envelope containing the various medicines is transferred to the patient so as to enable the patient to take the medicines.

In order to collect various medicines into one envelope, it is required that a medical person such as a pharmacist takes medicines prescribed to a patient out of respective containers such as bottles containing respective medicines and then put the medicines into the envelope. Therefore, it is necessarily required to execute a confirmation procedure of checking the accurate collection of medicines.

Hence, there is difficulty in ensuring an accurate dosage, and thus there is always the possibility of an incorrect medication administration accident. In addition to such an accident, a great deal of time is required to collect various medicines in order to fill a prescription for a patient because the work of collecting medicines is complicated, thereby deteriorating the efficiency of the collecting work, which is problematic.

For these reasons, research into automatic collection of various medicines from medicine containers has been continuously conducted. However, to date such efforts have been insufficient to satisfy both accuracy and efficiency of the collecting work, and it is thus still impossible to offer convenience to persons handling medicines.

SUMMARY OF THE INVENTION

Therefore, the present invention has been made in view of the above problems, and it is an object of the present invention to provide a medicine-dispensing apparatus capable of accurately and promptly dispensing desired medicines in response to a request for dispensation of medicines (for example, to fill prescription for a patient) and of maximizing the availability of space.

In accordance with an aspect of the present invention, the above and other objects can be accomplished by the provision of a medicine-dispensing apparatus including a medicine storage unit for separately containing a plurality of medicines, and a medicine transfer unit for receiving the plurality of medicines moved from the medicine storage unit in a first direction and transferring the plurality of medicines in a second direction, wherein the medicine transfer unit includes a frame unit on which the plurality of medicines are placed and a medicine-pushing unit movably disposed in the frame unit so as to transfer the plurality of medicines placed on the frame unit in the second direction, and wherein the medicine-pushing unit is able to be projected from and retracted into an internal space of the frame unit so as to move the plurality of medicines placed on the frame unit in the second direction.

The medicine-pushing unit may include a plurality of dividers for compartmenting the plurality of medicines placed on the frame unit, the plurality of dividers being arranged in a third direction, and each of the plurality of dividers may include a plurality of divider units spaced apart from each other in a second direction.

The frame unit may include a plurality of paths, which are formed in the second direction through the frame unit such that the plurality of divider units of the dividers are respectively projected from and retracted into the internal space through the plurality of paths.

A first divider unit of each of the plurality of dividers may serve to push a first medicine, disposed in a first space, to a second space that is located downstream of the first space, and a second divider unit of each of the plurality of dividers may serve to push the first medicine, moved to the second space, to a third space that is located downstream of the second space.

When the first medicine disposed in the first space is moved to the second space, the first and second divider units may be returned to initial positions at the time at which the first medicine M was disposed in the first space.

The medicine-pushing unit may dispense the plurality of medicines placed on the frame unit by continuous movement thereof due to the supply of power, and the plurality of medicines placed on the frame unit may be dispensed one by one by repetition of movement in the second direction for a predetermined period of time and halting for a predetermined period of time during continuous movement of the medicine-pushing unit.

The medicine-pushing unit may include a plurality of dividers for partitioning the plurality of medicines, and the plurality of dividers may be moved in the second direction so as to move the plurality of medicines placed on the frame unit in the second direction, may subsequently be retracted into the internal space, and may subsequently be returned to initial positions thereof after the lapse of the period of time taken by the halting.

The medicine-pushing unit may include a plurality of dividers for partitioning the plurality of medicines, each of the plurality of dividers may include a plurality of divider units, and a divider unit that is positioned at the furthest downstream among the plurality of divider units may have a height lower than that of remaining divider units.

The medicine-dispensing apparatus may further include a rotating unit, which is rotated by the supply of power so as to move the medicine-pushing unit, and the medicine-pushing unit may include a plurality of interlocking portions, which are spaced apart from each other so as to sequentially engage with the rotating unit.

The rotating unit may engage with the plurality of interlocking portions in sequence so as to move the medicine-pushing unit in the second direction.

The rotating unit may include a protrusion, and the medicine-pushing unit may include a fitting groove in which the protrusion of the rotating unit is fitted, wherein the fitting groove may include a forward groove section and a backward groove section, which extend in the second direction and are spaced apart from each other, and a hiding groove section and an exposing groove section, which connect the forward and backward groove sections to each other, such that the medicine-pushing unit is projected from and retracted into the internal space.

The protrusion may be provided at a center of the rotating unit.

The frame unit may be recessed in the first direction at at least part of a surface thereof on which the plurality of medicines are placed so as to prevent abnormal movement of the plurality of medicines during movement of the medicines in the second direction.

In accordance with another aspect of the present invention, there is provided a medicine-dispensing apparatus including a medicine storage unit for separately containing a plurality of medicines, and a medicine transfer unit for receiving the plurality of medicines moved from the medicine storage unit in a first direction and transferring the plurality of medicines in a second direction, wherein the medicine transfer unit includes a frame unit on which the plurality of medicines are placed and a medicine-pushing unit movably disposed in the frame unit so as to transfer the plurality of medicines placed on the frame unit in the second direction, wherein the medicine-pushing unit dispenses the plurality of medicines placed on the frame unit by continuous movement thereof due to the supply of power, and wherein the plurality of medicines placed on the frame unit are dispensed one by one by repetition of movement in the second direction for a predetermined period of time and halting for a predetermined period of time during continuous movement of the medicine-pushing unit.

In accordance with a further aspect of the present invention, there is provided a medicine-dispensing apparatus including a medicine storage unit for separately containing a plurality of medicines, and a medicine transfer unit for receiving the plurality of medicines moved from the medicine storage unit in a first direction and transferring the plurality of medicines in a second direction, wherein the medicine transfer unit includes a frame unit on which the plurality of medicines are placed and a medicine-pushing unit movably disposed in the frame unit so as to transfer the plurality of medicines placed on the frame unit in the second direction, wherein the medicine-pushing unit includes a plurality of dividers for compartmenting the plurality of medicines placed on the frame unit, each of the plurality of dividers including a plurality of divider units, and wherein a first divider unit of the plurality of divider units serves to push a first medicine, disposed in a first space, to a second space, which is located downstream of the first space, and a second divider unit of the plurality of divider units serves to push the first medicine, moved to the second space, to a third space, which is located downstream of the second space.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Hereinafter, specific embodiments of the present invention will be described with reference to the accompanying drawings. It will be obvious to those skilled in the art that the present invention is not limited to these embodiments, and various embodiments may be made by additions, changes and modifications without departing from the spirit and scope thereof. All such additions, changes and modifications should be construed as falling within the true spirit and scope of the present invention. Wherever possible, the same reference numbers will be used throughout the drawings to refer to the same or like parts.

Figure 1:
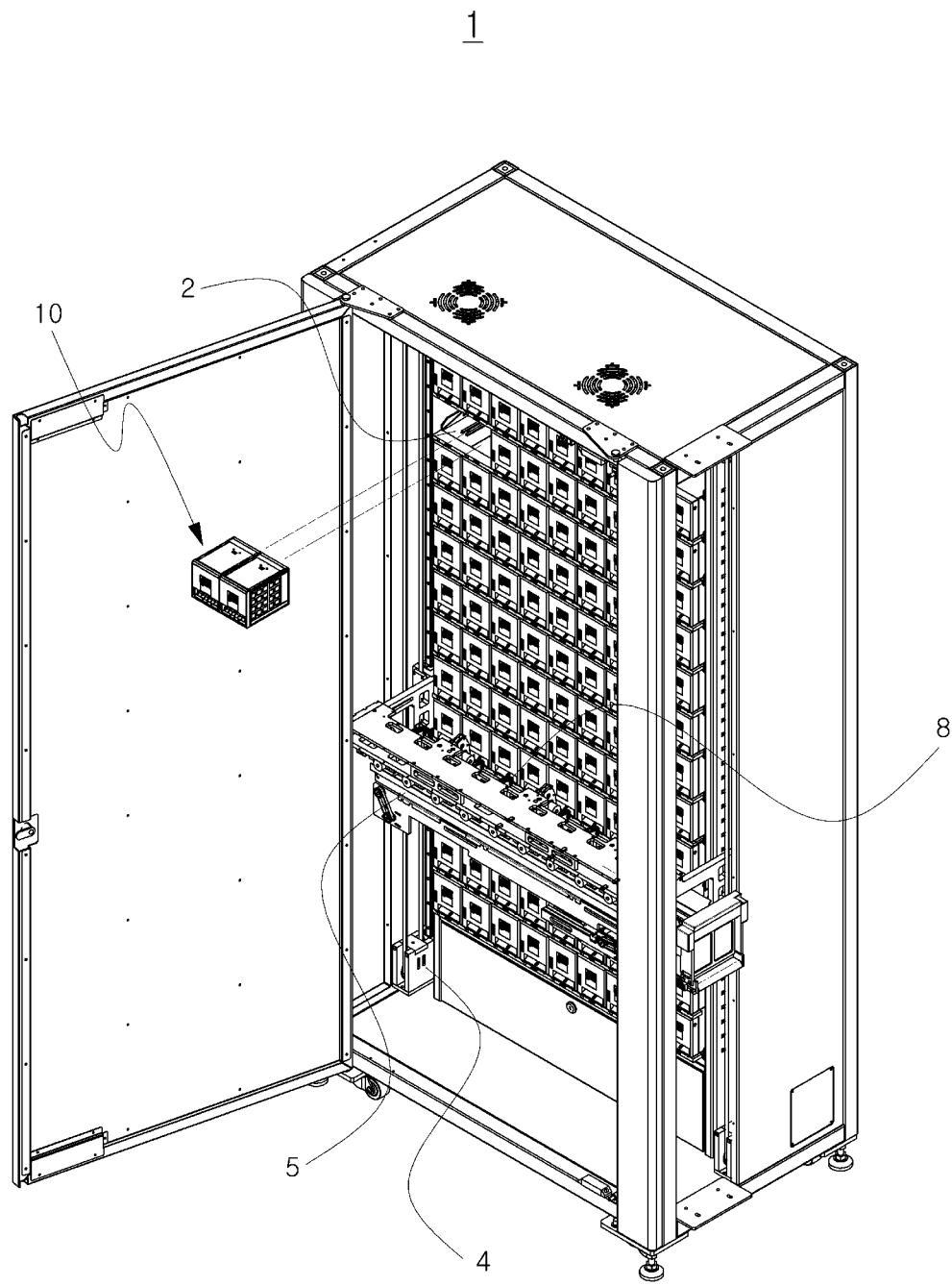
FIG. 1 is a schematic perspective view illustrating a medicine dispensing system including a medicine-dispensing apparatus according to an embodiment of the present invention.

FIG. 1 is a schematic perspective view illustrating a medicine dispensing system including a medicine-dispensing apparatus according to an embodiment of the present invention.

Referring to FIG. 1, the medicine dispensing system 1 according to the embodiment of the present may include a medicine-dispensing apparatus 10 for containing at least one medicine, a cartridge 2 through which the medicine-dispensing apparatus 10 can be mounted in the medicine dispensing system 1, a driving force supply 3 for supplying driving force required to dispense the medicines contained in the medicine-dispensing apparatus 10, and an inter-floor moving unit 4 for moving the driving force supply 3 between different floors in the medicine dispensing system 1.

In the medicine dispensing system 1 according to the embodiment of the present invention, a plurality of medicine-dispensing apparatuses 10 may be mounted on each of the cartridges 2, and the cartridges 2 may be respectively provided at the floors of the medicine dispensing system 1.

At least one cartridge 2 may be provided on each of the floors of the medicine dispensing system 1. The number of medicine-dispensing apparatuses 10 that are mounted on a single cartridge 2 may be variously changed depending on the intention of those skilled in the art.

The medicine dispensing system 1 may dispense a medicine by driving, that is, rotating, a dispensing unit 12 (see FIG. 2) of the medicine-dispensing apparatus 10 containing at least one medicine using the driving force supply 3. The medicine-dispensing apparatus 10 may be detachably mounted on the cartridge 2.

The medicine dispensed from the medicine-dispensing apparatus 10 may be placed on a conveyer unit 5. The medicine may be transferred to a predetermined external space and may be collected in the external space by rotational movement of the conveyer unit 5.

The movement of the driving force supply 3 between the floors may be realized by the inter-floor moving unit 4. The inter-floor moving unit 4 may move the driving force supply 3 to the floor at which the medicine-dispensing apparatus 10 containing a desired medicine is positioned, in response to an external signal.

In other words, when a signal corresponding to a prescription for a patient is applied to the medicine dispensing system 1 according to the embodiment of the present invention, the inter-floor moving unit 4 moves the driving force supply 3 to a desired floor, and a desired medicine may then be dispensed from the medicine-dispensing apparatus 10 by rotation of the dispensing unit 12 of the medicine-dispensing apparatus 10 by virtue of the driving force supply 3.

The dispensed medicine may be placed on the conveyer unit 5, and the conveyer unit 5 on which the medicine is placed may be moved to a position corresponding to a predetermined dispensing space by the inter-floor moving unit 4. Subsequently, the medicine may be collected in a predetermined external space by the rotational movement of the conveyer unit 5.

The embodiment is not necessarily limited to the case where the rotational movement of the conveyer unit 5 is performed after the conveyer unit 5 is moved to a position corresponding to a predetermined dispensing space. The rotational movement of the conveyer unit 5 may be performed before the conveyer unit 5 is moved to the position corresponding to the dispensing space.

When medicines according to a prescription for a patient are contained in a plurality of medicine-dispensing apparatuses 10 positioned at one floor or several floors, the driving force supply 3 may be moved to any one floor by the inter-floor moving unit 4, and medicines may be dispensed sequentially or concurrently from the plurality of medicine-dispensing apparatuses 10 disposed at that floor. After the completion of dispensation of the medicines at the one floor, the driving force supply 3 may be moved to another floor for further dispensation of medicines.

When the dispensation of the medicines from the plurality of medicine-dispensing apparatuses 10 according to the prescription for the patent is completed, the conveyer unit 5 with the plurality of medicines placed thereon may be moved to a position corresponding to a predetermined dispensing space by means of the inter-floor moving unit 4, and the plurality of medicines may then be collected in a predetermined external space by means of the rotational movement of the conveyer unit 5.

The driving force supply 3 for supplying the driving force required for the dispensation of medicines from the medicine-dispensing apparatus 10 is a component that may be omitted depending on the characteristics of the medicine-dispensing apparatus 10. In other words, in the case where the medicines contained in the medicine-dispensing apparatus 10 are dispensed by means of a separate component provided in the medicine-dispensing apparatus 10, the driving force supply 3 may be omitted.

When the driving force supply 3 is required in order to dispense medicines from the medicine-dispensing apparatus 10, the driving of the dispensing unit 12 by the driving force supply 3 may be controlled by a controller (not shown).

Furthermore, when dispensation of medicines from the medicine-dispensing apparatus 10 is performed by means of a separate component provided in the medicine-dispensing apparatus 10, the dispensation of medicines may also be controlled by the controller.

Figure 2:
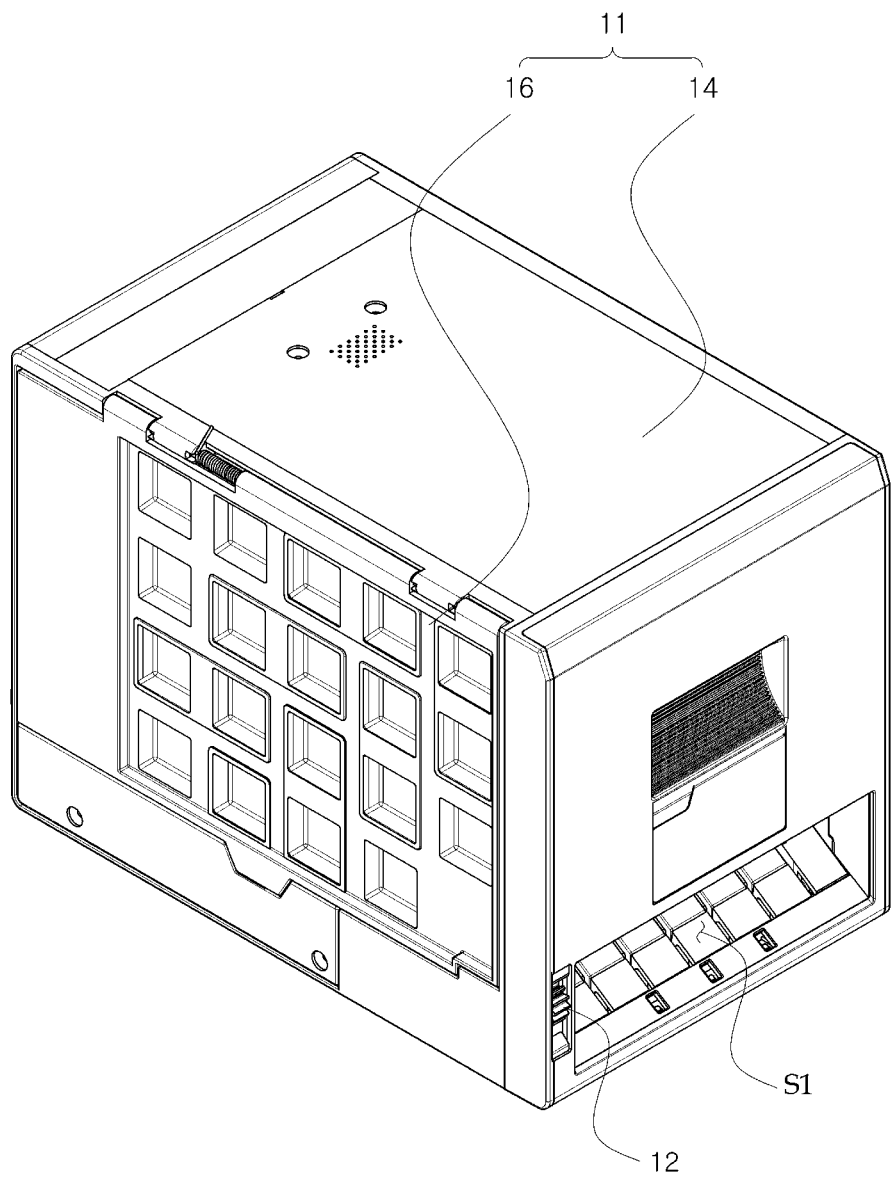
FIG. 2 is a schematic perspective view illustrating the medicine-dispensing apparatus according to the embodiment of the present invention.
Figure 3:
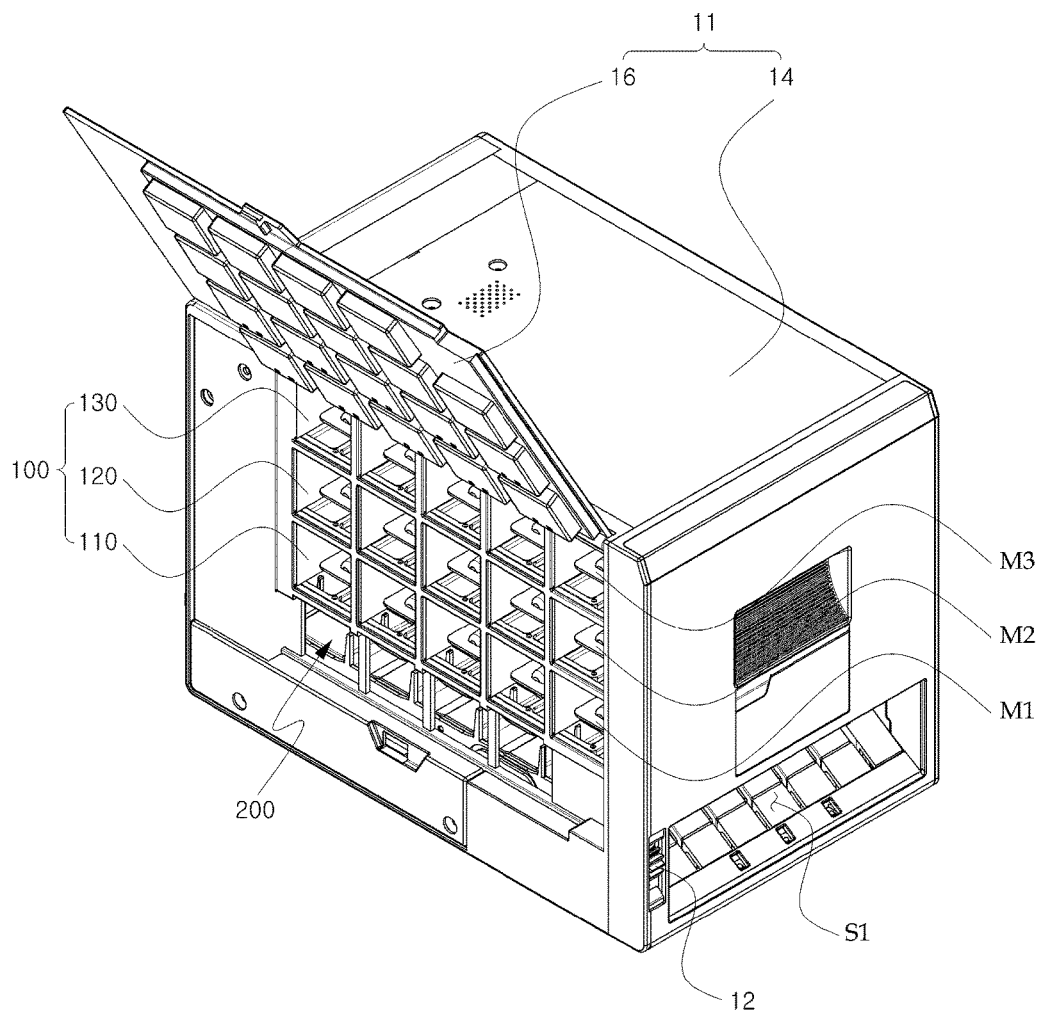
FIG. 3 is a schematic perspective view illustrating the medicine-dispensing apparatus according to the embodiment of the present invention, in which a cover is opened.

FIG. 2 is a schematic perspective view illustrating the medicine-dispensing apparatus 10 according to the embodiment of the present invention, and FIG. 3 is a schematic perspective view illustrating the medicine-dispensing apparatus 10 according to the embodiment of the present invention, in which a cover is opened.

Referring to FIGS. 2 and 3, the medicine-dispensing apparatus 10 according to the embodiment of the present invention may include medicine storage units 100, which are positioned at a plurality of floors so as to contain medicines, and a medicine transfer unit 200 for transferring medicines, which are moved from one of the medicine storage units 100, to a dispensing port S1.

The term "medicine" as used herein may refer to a tablet, a packaged powder drug, a pouch-type drug, an ampule, a vial or the like. However, the medicine is not necessarily limited thereto, and may also refer to a medical appliance such as a syringe.

For convenience of explanation, the drawings illustrate a plastic ampule as an example of the medicine.

The medicine storage units 100, which are positioned at a plurality of floors, may include a first medicine storage unit 110 to an Nth medicine storage unit (where N is a natural number). The first medicine storage unit 110 to the Nth medicine storage unit may be positioned sequentially from the lowermost floor to the uppermost floor of the medicine-dispensing apparatus 10.

Here, N may be, for example, 3, which is the case illustrated in FIGS. 2 and 3. However, N may be variously changed depending on the overall size of the medicine-dispensing apparatus 10, the size of the medicine contained in the medicine-dispensing apparatus 10, the type of medicine and the like.

Hereinafter, the case where N is 3 will be described.

The medicine-dispensing apparatus 10 may include a first medicine storage unit 110 for separately containing first medicines M1, a second medicine storage unit 120 for separately containing second medicines M2, a third medicine storage unit 130 for separately containing third medicines M3, and the medicine transfer unit 200, on which the first medicines M1 moved from the first medicine storage unit 110 are placed and which performs state change motion so as to transfer the first medicines M1 to the dispensing port S1.

The first medicine storage unit 110 to the third medicine storage unit 130 may be disposed in a housing 11 defining the appearance of the medicine-dispensing apparatus 10. The housing 11 may be configured so as to have, for example, a hexahedral shape.

The housing 11 may include a housing body 14 and a cover 16. The housing body 14 may be provided on the front face thereof with the dispensing port S, through which the first medicines M1 moved thereto by means of the medicine transfer unit 20 are discharged.

Furthermore, the housing body 14 may be provided on the front face thereof with the dispensing unit 12, which is in an exposed state and to which driving force is transmitted from the driving force supply 3 described with reference to FIG. 1.

The dispensing unit 12 may be omitted in the case where the dispensation of medicines is realized by a separate component provided in the medicine-dispensing apparatus 10, for example, a motor provided in the housing 11 so as to drive the medicine transfer unit 200, as described with reference to FIG. 1.

The cover 16 is swingably coupled at one side edge thereof to the housing body 14 so as to expose the first medicine storage unit 110 to the third medicine storage unit 130 to the outside or to close the same. Accordingly, the first medicines M1 to the third medicines M3 may be supplemented through the front face of the housing body 14, which is exposed by the opened cover 16.

In this regard, the opening motion of the cover 16 may be controlled by a lock device.

Figure 4:
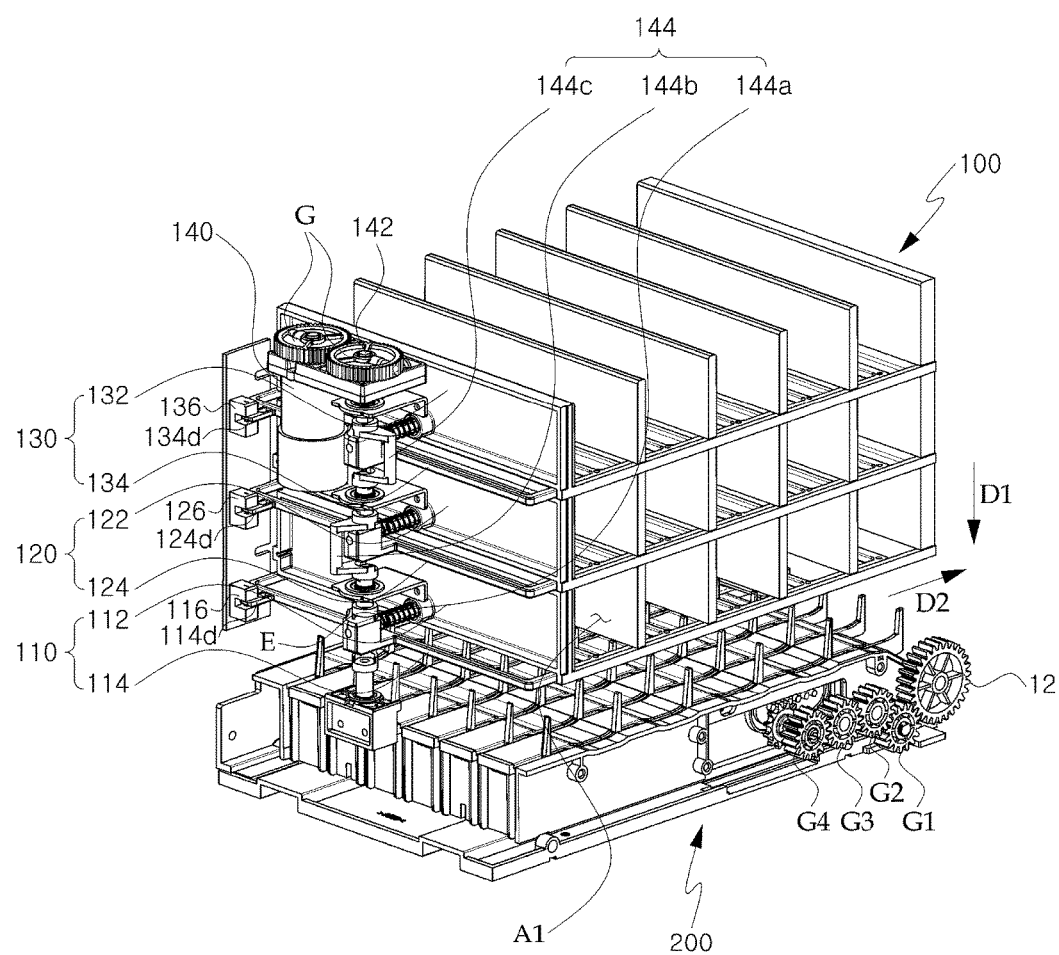
FIG. 4 is a view illustrating the internal structure of the medicine-dispensing apparatus according to the embodiment of the present invention.
Figure 5:
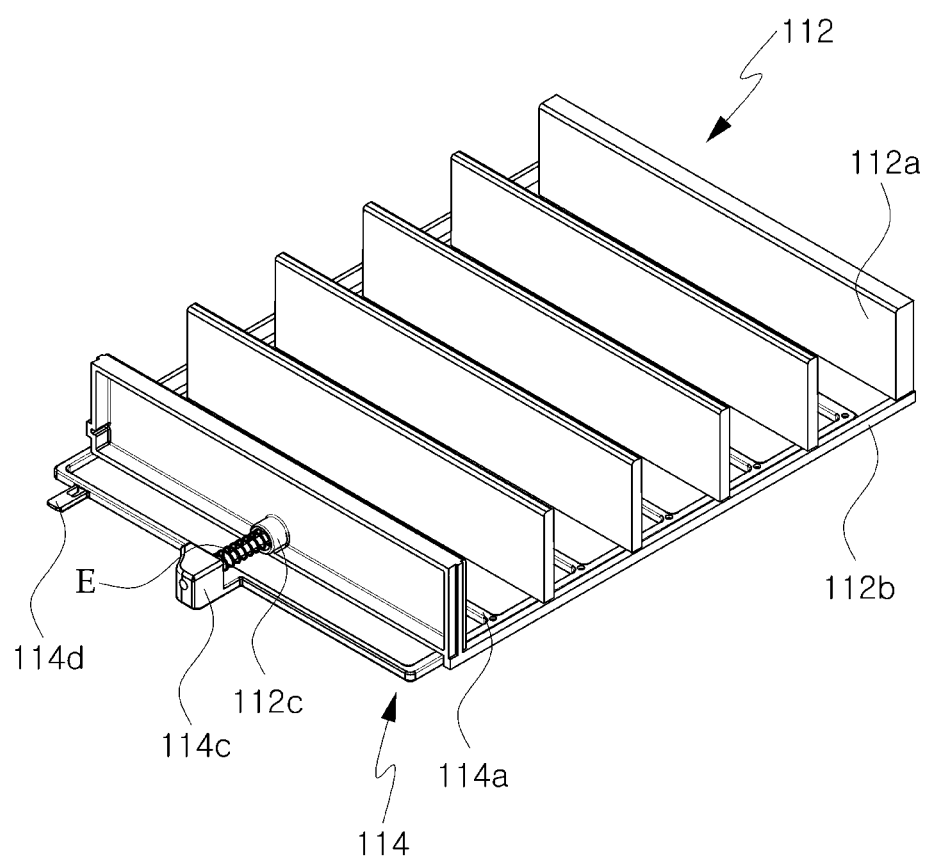
FIGS. 5 and 6 are views illustrating the medicine storage unit provided in the medicine-dispensing apparatus 10 according to the embodiment of the present invention.
Figure 6:
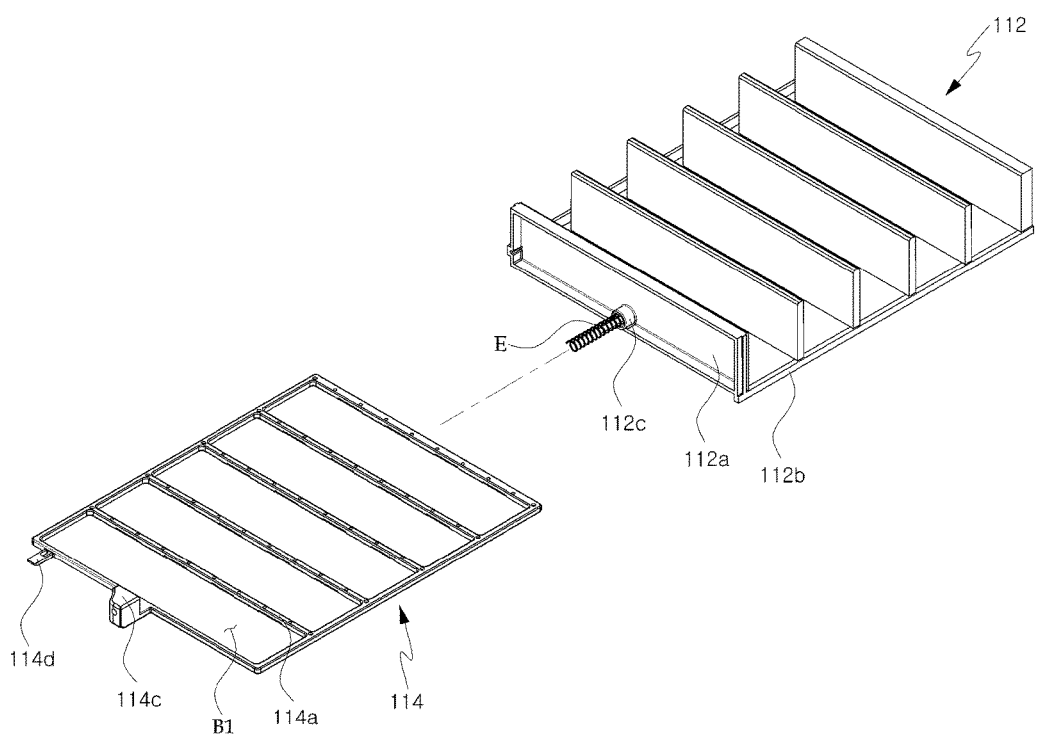

FIG. 4 is a view illustrating the internal structure of the medicine-dispensing apparatus according to the embodiment of the present invention, and FIGS. 5 and 6 are views illustrating the medicine storage unit provided in the medicine-dispensing apparatus 10 according to the embodiment of the present invention.

Figure 7:
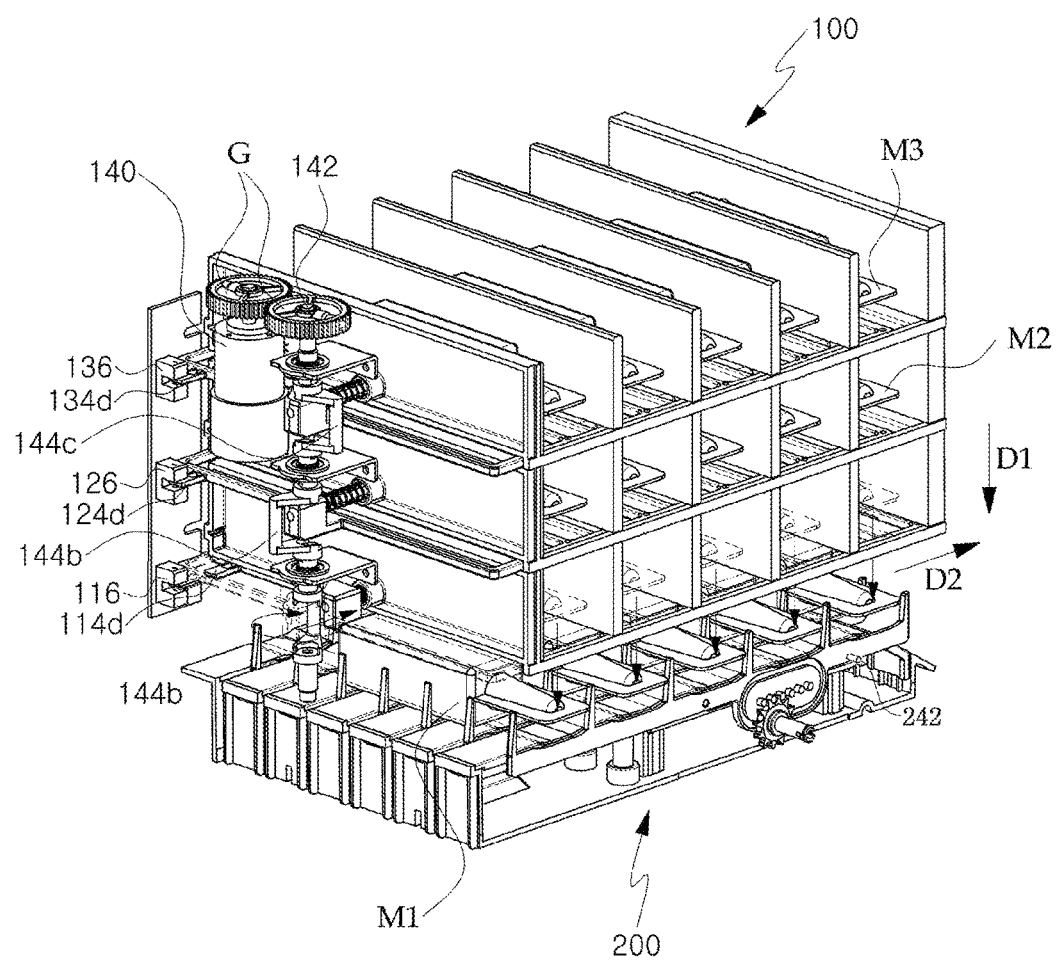
FIGS. 7 and 8 are views illustrating the principle whereby medicines are moved to the medicine transfer unit from the medicine storage unit, which is provided in the medicine-dispensing apparatus according to the embodiment of the present invention.
Figure 8:
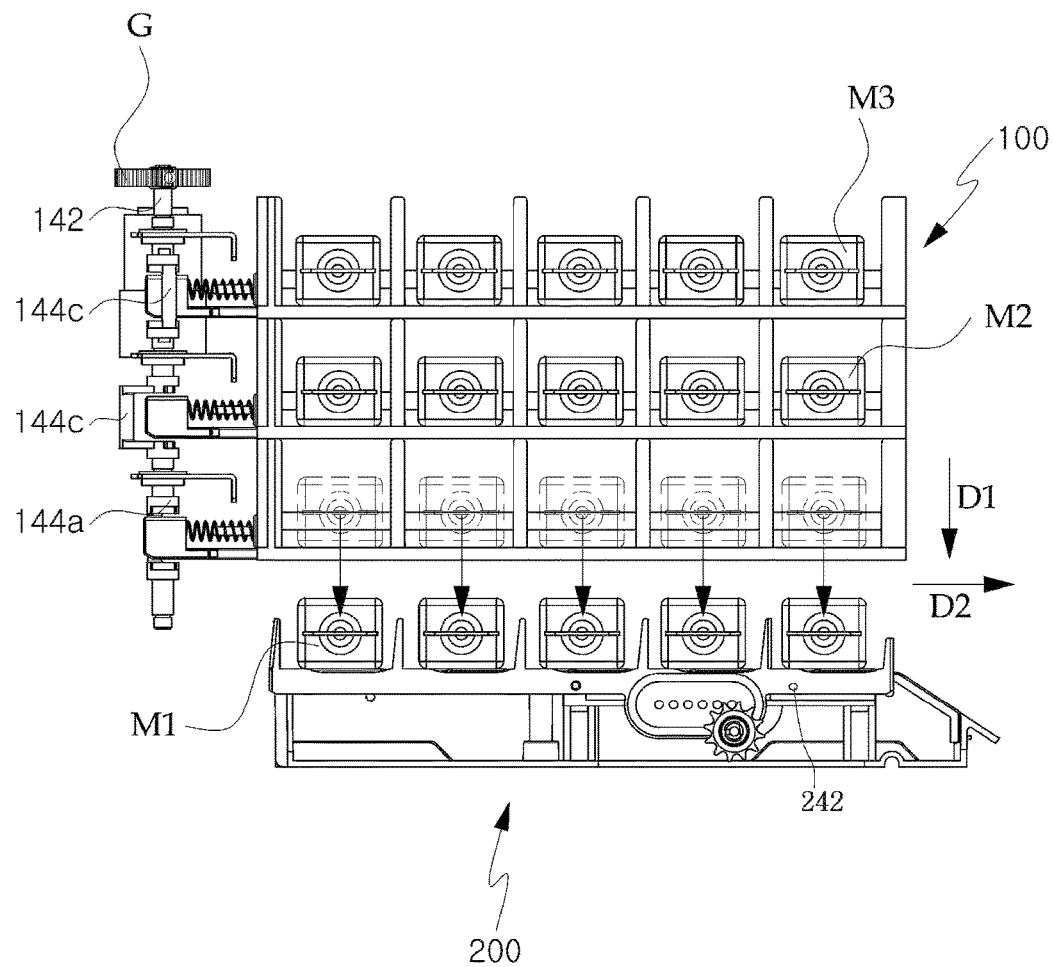

FIGS. 7 and 8 are views illustrating the principle whereby medicines are moved to the medicine transfer unit from the medicine storage unit, which is provided in the medicine-dispensing apparatus 10 according to the embodiment of the present invention.

Referring to FIGS. 4 to 8, the medicine-dispensing apparatus 10 according to the embodiment of the present invention may include the medicine storage units 100 for separately containing a plurality of medicines M1, M2 and M3, and the medicine transfer unit 200, which receives the plurality of medicines M1, M2 and M3 moved from the medicine storage unit 100 in the first direction D1 and transfers the plurality of medicines M1, M2 and M3 in the second direction D2.

For example, the medicine storage units 100 may include the first medicine storage unit 110 for separately containing the first medicines M1, the second medicine storage unit 120 for separately containing the second medicines M2 and the third medicine storage unit 130 for separately containing the third medicines M3.

The medicine transfer unit 200 receives the first medicines M1 moved from the first medicine storage unit 110 in the first direction D1 and transfers the received first medicines M1 to the dispensing port S1.

The first medicines M1, the second medicines M2 and the third medicines M3 may be the same kind of medicines. However, the first to third medicines may be different kinds of medicines, and the first medicines M1 may include different kinds of medicines.

The first medicine storage unit 110, the second medicine storage unit 120 and the third medicine storage unit 130 may be sequentially disposed from the lowermost floor of the housing 11 in the direction opposite the first direction D1.

In other words, the medicine-dispensing apparatus 10 according to the embodiment of the present invention enables the medicines M1, M2 and M3 to be dispensed through the dispensing port S1 by the state change motion of the medicine transfer unit 200. The first medicine storage unit 110, the second medicine storage unit 120 and the third medicine storage unit 130 may serve as waiting spaces for dispensation, which temporarily store the medicines dispensed by the medicine transfer unit 200.

When it is required to dispense the desired medicines according to a prescription for patient while the medicine-dispensing apparatus 10, in which the first medicines M1, the second medicines M2 and the third medicines M3 are respectively contained in the first medicine storage unit 110, the second medicine storage unit 120 and the third medicine storage unit 130, is mounted in the cartridge (see FIG. 1), the first medicines M1 contained in the first medicine storage unit 110 may first be moved to the medicine transfer unit 200.

Thereafter, the second medicines M2 contained in the second medicine storage unit 120 may be moved to the first medicine storage unit 110, and the third medicines M3 contained in the third medicine storage unit 130 may then be moved to the second medicine storage unit 120.

Consequently, the medicine-dispensing apparatus 10 according to the embodiment of the present invention enables the second medicines M2 and the third medicines M3 to be sequentially dispensed to the outside through the dispensing port S1 by means of the medicine transfer unit 200 while or after the first medicines M1 contained in the first medicine storage unit 110 are dispensed to the outside through the dispensing port S1 by means of the medicine transfer unit 200.

As illustrated in FIGS. 7 and 8, the movement of the first medicines M1 from the first medicine storage unit 110 to the medicine transfer unit 200 may be realized by positional change of a first control unit 114, the movement of the second medicines M2 from the second medicine storage unit 120 to the first medicine storage unit 110 may be realized by positional change of a second control unit 124 with respect to a second storage body 122, and the movement of the third medicines M3 from the third medicine storage unit 130 to the second medicine storage unit 120 may be realized by positional change of a third control unit 134 with respect to a third storage body 132.

Since the first medicine storage unit 110, the second medicine storage unit 120 and the third medicine storage unit 130 have the same structure, only the first medicine storage unit 110 will hereinafter be described, and descriptions of the second medicine storage unit 120 and the third medicine storage unit 130 are omitted.

As illustrated in the drawings, the first medicine storage unit 110 may include a first storage body 112 and a first control unit 114. The first storage body 112 may include first side walls 112a defining first storage spaces A1 and a connecting wall 112b connecting the first side walls 112a to each other so that the first medicines M1 are separately contained in the first storage spaces A1.

One of the first side walls 112a, which is positioned at a lateral side of the first storage body 112, may be provided with a holder 112c for receiving or holding at least part of an elastic element E, which is a kind of spring.

The control unit 114, which is able to be changed in position, is disposed under the first connecting wall 112b.

The first control unit 114 may include first passages B1, through which the first medicines M1 contained in the first storage spaces A1 pass, and a first definition frame 114a defining the boundaries of the first passages B1. The first definition frame 114a may be provided at a side edge thereof with a counter holder 114c for receiving or holding the elastic element E.

As illustrated in FIG. 4, the first definition frame 114a may support the first medicines M1 before the first medicines M1 pass through the passages B1. As illustrated in FIGS. 7 and 8, when the first definition frame 114a is positioned under and thus aligned with the first side walls 112a by the positional change of the first control unit 114, the first medicines M1 contained in the first storage spaces A1 fall onto the medicine transfer unit 200 through the first passages B1 in the first direction D1.

The positional change of the first control unit 114 may be realized by means of various components, for example, by means of members capable of being rotated by the driving force from a driving motor 140.

Specifically, the positional change of the first control unit 114 may be realized by means of a rotating shaft 142, which is rotated by driving force from the driving motor 140, and a striker 144, which is rotated by the rotation of the rotating shaft 142.

The driving force from the driving motor 140 may be transmitted to the rotating shaft 142 through driving gears G. Accordingly, as the rotating shaft 142 is rotated, the first striker 144a, the second striker 114b and the third striker 144c are sequentially brought into contact with the first control unit 114, the second control unit 124 and the third control unit 134, respectively, thereby causing the positional change of the control units.

Consequently, by the rotation of the rotating shaft 142, the first medicines M1 contained in the first medicine storage unit 110 may fall onto the medicine transfer unit 200, the second medicines M2 contained in the second medicine storage unit 120 may fall onto the first medicine storage unit 110, and the third medicines M3 contained in the third medicine storage unit 130 may fall onto the second medicine storage unit 120.

Here, when the first striker 144a is brought into contact with the first control unit 114, the position of the first control unit 114 is changed so that the first medicines M1 contained in the first medicine storage unit 110 fall onto the medicine transfer unit 200. As the first striker 144a is further rotated, the first control unit 114 is returned to its initial position by the restoring force of the elastic element E.

Subsequently, the second striker 144b is brought into contact with the second control unit 124 so as to change the position of the second control unit 124, thereby allowing the second medicines M2 to fall onto the first medicine storage unit 110.

Consequently, by the rotation of the rotating shaft 142 caused by the driving force supplied from the single driving source, that is, the driving motor 140, the positions of the first control unit 114 and the second control unit 124 may be changed at a time interval.

Meanwhile, the positional change of the first control unit 114 caused by the first striker 144a, which is rotated by the rotation of the rotating shaft 142, the positional change of the second control unit 124 caused by the second striker 144b and the positional change of the third control unit 134 caused by the third striker 144c may be respectively detected by a first sensor 116, a second sensor 126 and a third sensor 136.

The first sensor 116, the second sensor 126 and the third sensor 136 may be disposed on the inner surface of the housing body 14 so as to respectively detect the position of a first projection 114d formed at a side edge of the first control unit 114, the position of a second projection 124d formed at a side edge of the second control unit 124, and the position of a third projection 134d formed at a side edge of the third control unit 134.

Accordingly, the movement of the first medicines M1 from the first medicine storage unit 110 to the medicine transfer unit 200, the movement of the second medicines M2 from the second medicine storage unit 120 to the first medicine storage unit 110 and the movement of the third medicines M3 from the third medicine storage unit 130 to the second medicine storage unit 120 may be respectively detected by the first sensor 116, the second sensor 126 and the third sensor 136.

The principle whereby the first medicines M1, which are moved to the medicine transfer unit 200 from the first medicine storage unit 110, are dispensed to the outside through the dispensing port S1 will be described hereinafter.

Figure 9:
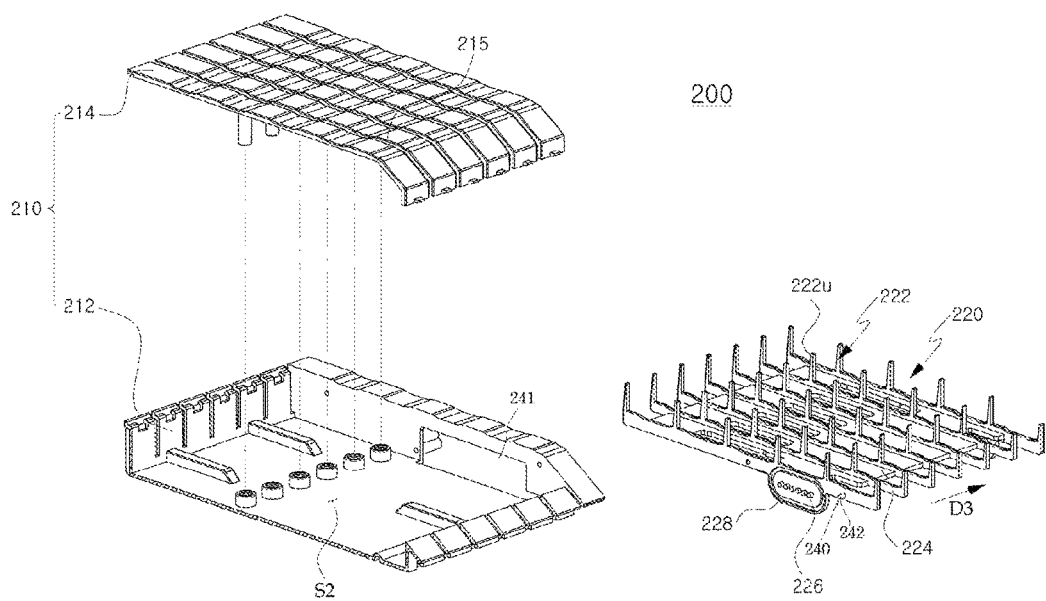
FIGS. 9 and 10 are views illustrating the medicine transfer unit provided in the medicine-dispensing apparatus according to the embodiment of the present invention.
Figure 10:
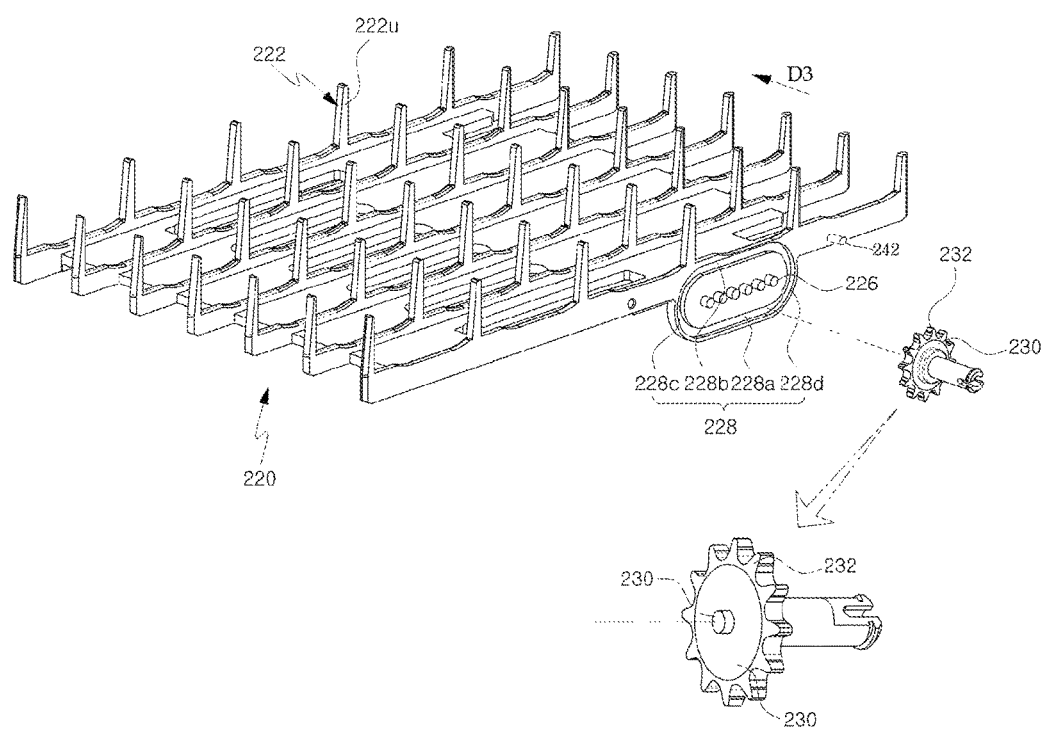
Figure 11:
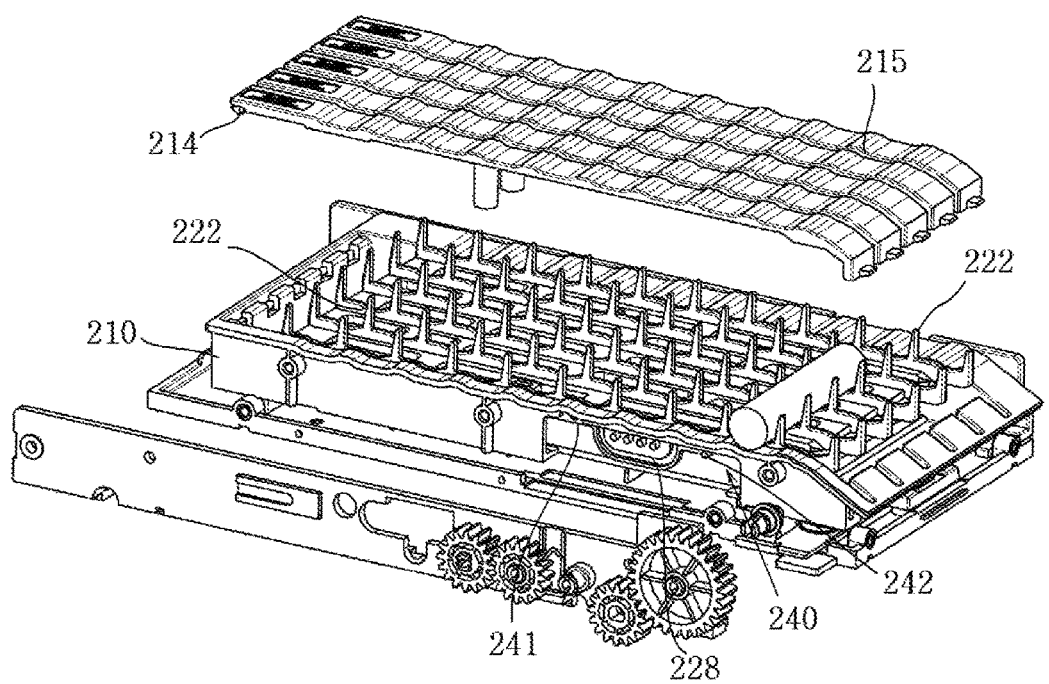
FIG. 11 is an exploded perspective view illustrating a separation-prevention unit according to the present invention.

FIGS. 9 and 10 are views illustrating the medicine transfer unit 200 provided in the medicine-dispensing apparatus 10 according to the embodiment of the present invention, and FIG. 11 is an exploded perspective view illustrating a separation-prevention unit according to the present invention. FIGS. 12 to 14 are views illustrating the principle whereby medicines are transferred by the medicine transfer unit 200 provided in the medicine-dispensing apparatus 10 according to the embodiment of the present invention.

Referring to FIGS. 9 to 14, the medicine transfer unit 200 provided in the medicine-dispensing apparatus 10 may include a frame unit 210, on which a plurality of medicines M are placed, and a medicine-pushing unit 220, which is movably disposed in the frame unit 210 so as to move the plurality of medicines M placed on the frame unit 210 in the second direction D2.

The medicine-pushing unit 220 may be projected from the internal space S2 of the frame unit 210 so as to move the plurality of medicines M placed on the frame unit 210 in the second direction D2.

The frame unit 210 may include a space-defining part 212 defining the internal space S2 therein, and a path-defining part 214, which covers the open upper face of the space-defining part 212 and which has paths 215 through which the medicine-pushing unit 220 is projected to the outside.

The path-defining part 214 may include a plurality of path-defining parts, and the paths 215 may be defined between the path-defining parts 214.

The path-defining part 214 does not necessarily need to include the plurality of path-defining parts 214, and may be embodied as a single component. In this case, the paths may be formed by slitting the single component at predetermined intervals.

Consequently, the frame unit 210 may include the plurality of paths 215, which are formed in the second direction D2, so that the medicine-pushing unit 220 is projected from the internal space S2.

The medicine-pushing unit 220 may include a plurality of dividers 222 serving to compartment the plurality of medicines M placed on the frame unit 210. Each of the dividers 222 may include a plurality of divider units 222u, which are spaced apart from each other in the second direction D2.

The plurality of divider units 222u may be projected from the internal space S2 through the paths 215.

The plurality of dividers 222 may be integrally connected to each other via connectors 224. The plurality of dividers 222 may push the medicines M toward the dispensing port S1.

Referring again to FIG. 1, when a signal according to a prescription for a patient is applied to the medicine dispensing system 1 according to the embodiment of the present invention, the inter-floor moving unit 4 moves the driving force supply 3 to a desired floor in response to the signal.

Subsequently, the driving force supply 3 rotates the dispensing unit 12 of the medicine-dispensing apparatus 10.

Upon rotation of the dispensing unit 12, a first gear G1 (see FIG. 4), a second gear G2 (see FIG. 4), a third gear G3 (see FIG. 4) and a fourth gear G4 (see FIG. 4) are rotated, and a gear-shaped rotating unit 230 mounted on a common shaft, on which the fourth gear G4 is mounted, is in turn rotated.

The rotating unit 230 may be a component that is rotated by rotation of the fourth gear G4, that is, by a specific power, so as to move the medicine-pushing unit 220. The medicine-pushing unit 220 may include a plurality of interlocking portions 226, which are spaced apart from each other in the second direction D2 such that the medicine-pushing unit 220 is moved in conjunction with the rotating unit 230.

The plurality of interlocking portions 226 may be formed on a side surface of the medicine-pushing unit 220. As the rotating unit 230 is rotated, the rotating unit 230 sequentially engages with the plurality of interlocking portions 226 so as to move the medicine-pushing unit 220 in the second direction D2 or in the direction opposite the second direction D2.

The projection of the medicine-pushing unit 220 from the internal space S2 may be realized by cooperation between a center protrusion 232 of the rotating unit 230 and a fitting groove 228 of the medicine-pushing unit 220.

The center protrusion 232 may project from the center of the rotating unit 230.

The fitting groove 228 may be formed so as to be recessed into the medicine-pushing unit 220, and may include a forward groove 228a and a backward groove 228b, which extend in the second direction D2 in the state of being spaced apart from each other, and a hiding groove section 228c and an exposing groove section 228d, which connect the forward groove section 228a and the backward groove section 228b to each other.

The hiding groove section 228c and the exposing groove section 228d may be configured to be rounded.

Hereinafter, the principle whereby the medicines M are moved to the dispensing port S1 by means of the medicine-pushing unit 220 will be described in detail. Specifically, the principle whereby the medicines M disposed in a first space B1 are sequentially moved to a second space B2 and a third space B3, which are located downstream of the first space B1, will be described, for convenience of explanation.

Figure 12A:
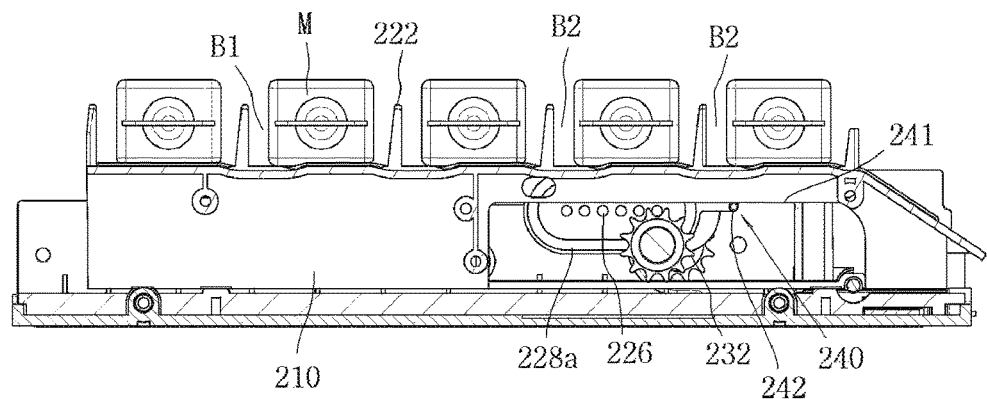
FIGS. 12A, 12B, 13A, 13B, 14A, 14B, and 14C are views illustrating the principle whereby medicines are transferred by the medicine transfer unit provided in the medicine-dispensing apparatus according to the embodiment of the present invention.
Figure 12B:
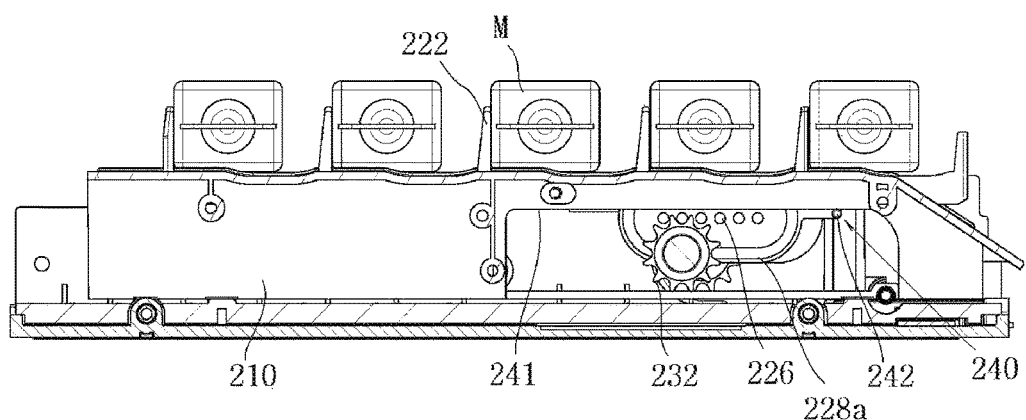

Referring to FIGS. 12A and 12B, a first divider unit 222u of each of the plurality of dividers 222 may push the medicine M disposed in the first space B1 on the frame unit 210 by sequential change of the interlocking portions 226 engaging with the rotating unit 230 during rotation of the rotating unit 230.

At this point, the center protrusion 232 may be disposed in the forward groove section 228a. The first divider unit 222u is moved forward by the sequential change of the interlocking portions 226 engaging with the rotating unit 230, and the medicine M disposed in the first space B1 is thus moved toward the second space B2.

Figure 13A:
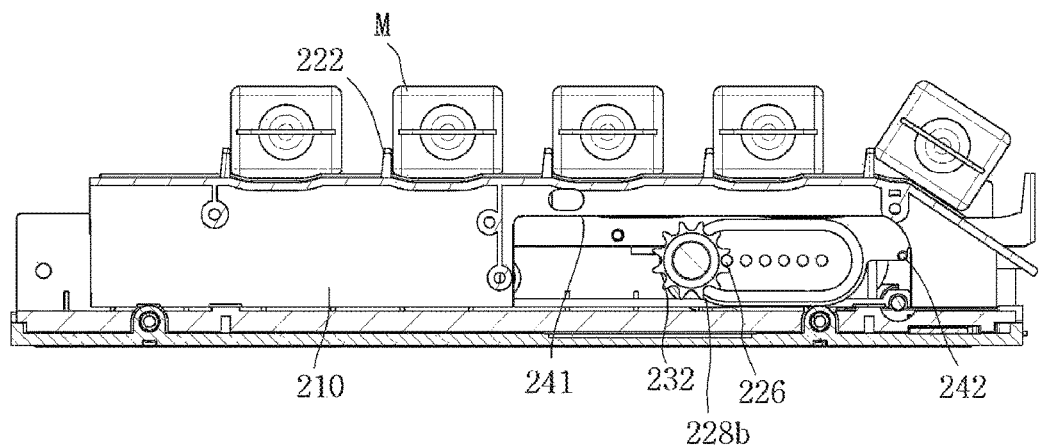
Figure 13B:
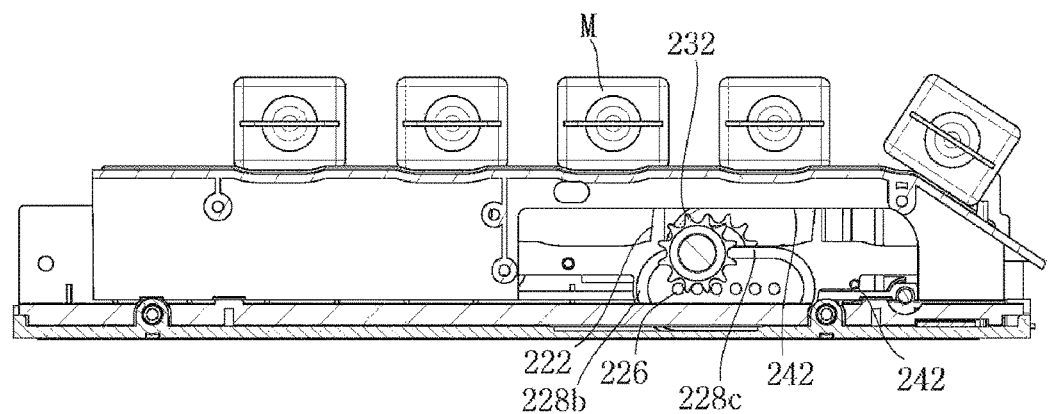

Subsequently, as the rotating unit 230 is further rotated, the center protrusion 232 is introduced into the hiding groove section 228b, as illustrated in FIGS. 13A and 13B.

At this point, the rotating unit 230 engages with the rearmost one of the interlocking portions 226, and the center protrusion 232 is introduced into the hiding groove section 228c. Consequently, the first divider unit 222u is retracted into the internal space S2.

Figure 14A:
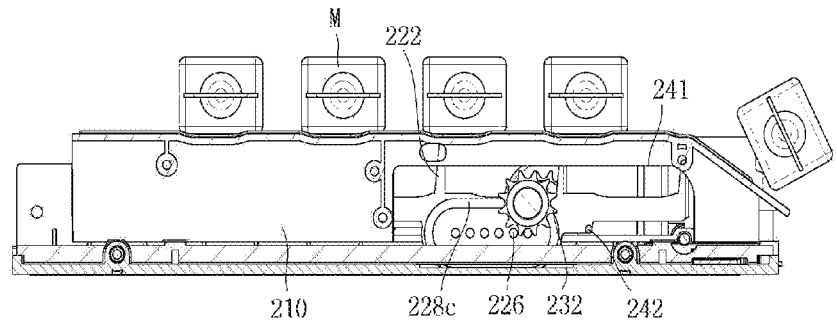

Subsequently, as the rotating unit 230 is further rotated, the center protrusion 232 is introduced into the backward groove section 228b, as illustrated in FIG. 14A.

At this point, the first divider unit 222u is moved in the direction opposite the second direction D2 due to the sequential change of the interlocking portions 226 engaging with the rotating unit 230. In other words, the first divider unit 222u is moved rearward in the state of being hidden in the internal space S2.

Figure 14B:
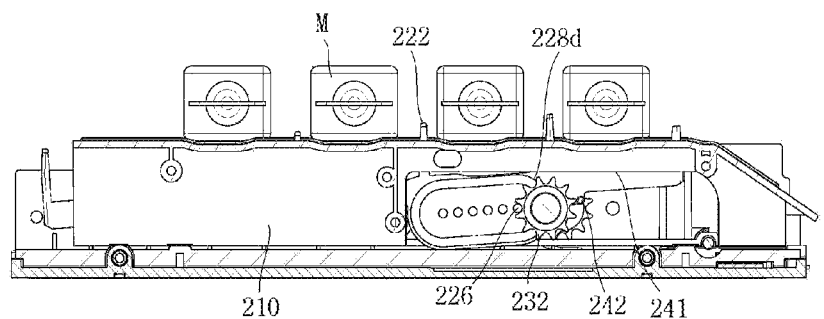
Figure 14C:
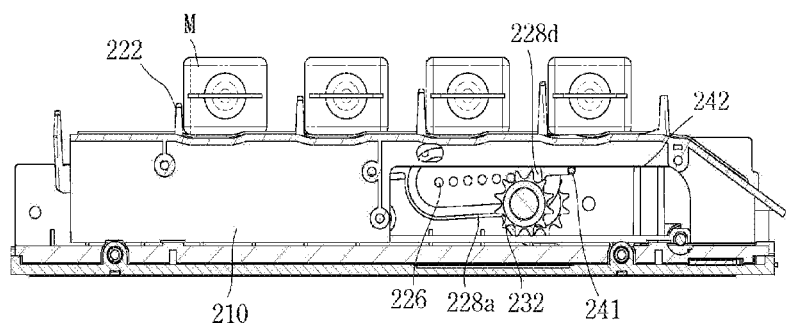

Subsequently, as the rotating unit 230 is further rotated, the center protrusion 232 is introduced into the exposing groove section 228d, as illustrated in FIG. 14B.

At this point, the rotating unit 230 engages with the foremost one of the interlocking portions 226, and the first divider unit 222u is exposed from the internal space S2 due to the rounded exposing groove section 228d.

Subsequently, the first divider unit 222u is finally returned to the position shown in (a) of FIG. 12.

As the procedure illustrated in FIG. 12A to FIG. 14C is repeated, the second divider unit 222u, which is located downstream of the first divider unit 222u, pushes the medicine M that has been moved to the second space B2 from the first space B1, thereby transferring the medicine M to the third space B3 from the second space B2.

As a result, the medicine M disposed in the first space B1 is finally dispensed to the outside through the dispensing port S1 by the above-described procedure.

When the medicine M disposed in the first space B1 is moved to the second space B2, the first divider unit 222u and the second divider unit 222u may be returned to the initial positions at the time at which the medicine M was disposed in the first space B1.

Although the medicine-pushing unit 220 is continuously moved, the plurality of medicines M placed on the path-defining part 214 of the frame unit 210 may be dispensed one by one by repetition of the movement of the medicines M in the second direction D2 for a predetermined period of time and the halting of the medicines M for a predetermined period of time.

This repeated motion is realized by the hiding groove section 228c, the backward groove section 228b and the exposing groove section 228d of the fitting groove 228. Specifically, because the forward groove section 228a and the backward groove section 228b have almost the same length, the period of time that the movement of the medicine is halted may be longer than the period of time that the medicine M is moved in the second direction D2 due to the presence of the hiding groove section 228c and the exposing groove section 228d.

The first divider unit 222u and the second divider unit 222u are moved in the second direction D2 so as to move the plurality of medicines placed on the path-defining part 214 in the second direction D2, are subsequently retracted into the internal space S2, and are subsequently returned to the initial position after the halting for a predetermined period of time.

The divider unit 222u that is positioned at the furthest downstream among the plurality of divider units 222u may have a height lower than that of other divider units 222u.

The reason for this is because the downstream end of the path-defining part 214 is inclined downward so that the internal space in the downstream end is smaller than the remaining region of the path-defining part 214.

In other words, since the divider unit 222u that is positioned at the furthest downstream has a height lower than that of the other divider units 222u, the present invention is able to prevent the medicines M from being caught by the divider units 222u when passing through the dispensing port S1.

In order to prevent abnormal movement of the plurality of medicines M during the movement in the second direction D2, the path-defining part 214 of the frame unit 210 may be recessed in the first direction D1 at at least part of the surface thereof on which the medicines M are placed.

The term "abnormal movement" as used herein may refer to movement in which a medicine placed on a specific location on the path-defining part 214 is moved to another position when the divider unit 222u is retracted into the internal space S2.

Consequently, since the path-defining part 214 is recessed at at least part thereof such that a medicine M is stably placed in the recessed portion, it is possible to prevent the abnormal movement of medicine M which would otherwise occur when the divider unit 222u is retracted into the internal space S2.

Furthermore, the medicine-dispensing apparatus 10 according to the embodiment of the present invention may include a separation-prevention unit 240 for restricting the range of upward projection of the medicine-pushing unit 220 during the movement of the medicine-pushing unit 220.

As illustrated in FIG. 11, the separation-prevention unit 240 includes a rectangular guide hole 241, which is formed in a lateral side of the frame unit 20 so as to open downward, and an engagement protrusion 242, which is provided on a lateral surface of the medicine-pushing unit 220 near to the fitting groove 228 so as to be engaged with the upper side of the guide hole 241, thereby restricting the range of the upward projection of the medicine-pushing unit 220.

Furthermore, the medicine-dispensing apparatus 10 according to the embodiment of the present invention may include a fourth sensor (not shown) for detecting the projection and retraction of the medicine-pushing unit 220 with respect to the internal space S2 of the frame unit 210.

The fourth sensor may be embodied as one of various sensors, for example, a sensor for detecting magnetic force.

Figure 15A:
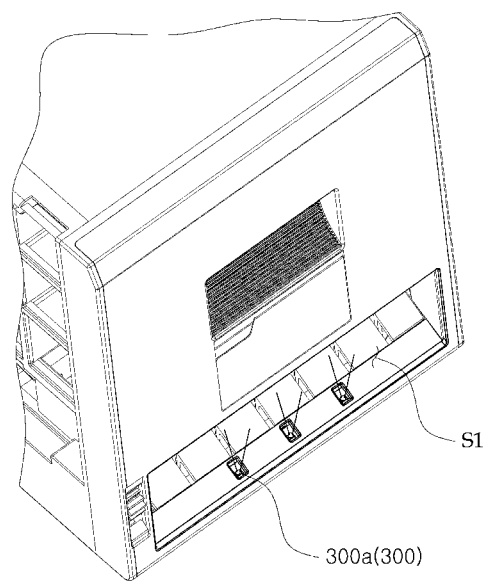
FIGS. 15A and 15B are views illustrating the principle whereby dispensation of medicines from medicine-dispensing apparatus according to the embodiment of the present invention is detected.
Figure 15B:
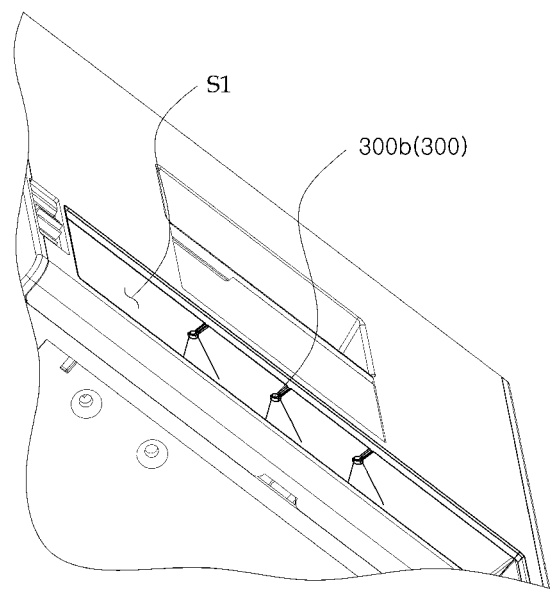

FIGS. 15A and 15B are views illustrating the principle whereby the dispensation of medicines from the medicine-dispensing apparatus 10 according to the embodiment of the present invention is detected.

Referring to FIGS. 15A and 15B, when the medicines M pass through the dispensing port S1 by the state change motion of the medicine transfer unit 200, the passage of medicines M may be detected by a fifth sensor 300.

The fifth sensor 300 may include a light-emitting element 300a and a light-receiving element 300b. The light-emitting element 300a may continuously emit light toward the light-receiving element 300b.

In this case, since the path of light between the light-emitting element 300a and the light-receiving element 300b is instantaneously interrupted when the medicines M pass through the dispensing port S1, the dispensation of the medicines M may be detected by the instantaneous interruption of the path of light.

As is apparent from the above description, the medicine-dispensing apparatus according to the embodiment of the present invention is able to accurately and promptly dispense desired medicines in response to a request for the dispensation of medicines (for example, a prescription for a patient).

In addition, the medicine-dispensing apparatus according to the embodiment of the present invention can be made compact by maximizing the availability of space for accommodating medicines.

Although the preferred embodiments of the present invention have been disclosed for illustrative purposes, those skilled in the art will appreciate that various modifications, additions and substitutions are possible, without departing from the scope and spirit of the invention as disclosed in the accompanying claims. Such modifications, additions and substitutions are intended to fall within the scope of the present invention and the appended claims.

For example, the means for providing or transmitting power required to rotate the rotating unit 230 is not limited to the dispensing unit 12, the first gear G1, the second gear G2 or the like, and may also be embodied as a belt or a self-driving device.

What is claimed is:

1. A medicine-dispensing apparatus comprising:
   a medicine storage assembly for separately containing a plurality of medicines; and
   a medicine transfer assembly for receiving the plurality of medicines moved from the medicine storage assembly in a first direction and transferring the plurality of medicines in a second direction,
   wherein the medicine transfer assembly includes a frame assembly on which the plurality of medicines are placed and a medicine-pushing assembly movably disposed in the frame assembly so as to transfer the plurality of medicines placed on the frame assembly in the second direction, and
   wherein the medicine-pushing assembly is configured to be projected from and retracted into an internal space of the frame assembly so as to move the plurality of medicines placed on the frame assembly in the second direction,
   wherein the apparatus further comprises a rotating unit, which is rotated by a power supply so as to move the medicine-pushing assembly,
   wherein the medicine-pushing assembly includes a plurality of interlocking portions, which are spaced apart from each other so as to sequentially engage with the rotating assembly,
   wherein the rotating assembly engages with the plurality of interlocking portions in sequence so as to move the medicine-pushing assembly in the second direction,
   wherein the rotating assembly includes a protrusion, and the medicine-pushing assembly includes a fitting groove in which the protrusion of the rotating assembly is fitted, and
   wherein the fitting groove includes a forward groove section and a backward groove section, which extend in the second direction and are spaced apart from each other, and a hiding groove section and an exposing groove section, which connect the forward and backward groove sections to each other, such that the medicine-pushing assembly is projected from and retracted into the internal space.

2. The medicine-dispensing apparatus according to claim 1, wherein the medicine-pushing assembly includes a plurality of dividers for compartmenting the plurality of medicines placed on the frame assembly, the plurality of dividers being arranged in a third direction,
   wherein each of the plurality of dividers includes a plurality of divider parts spaced apart from each other in the second direction.

3. The medicine-dispensing apparatus according to claim 2, wherein the frame assembly includes a plurality of paths, which are formed in the second direction through the frame assembly such that the plurality of divider parts of the dividers are respectively projected from and retracted into the internal space through the plurality of paths.

4. The medicine-dispensing apparatus according to claim 2, wherein a first divider part of the plurality of divider parts serves to push a first medicine, disposed in a first space, to a second space that is located downstream of the first space, and a second divider part of the plurality of divider parts serves to push the first medicine, moved to the second space, to a third space that is located downstream of the second space.

5. The medicine-dispensing apparatus according to claim 4, wherein, when the first medicine disposed in the first space is moved to the second space, the first and second divider parts are returned to initial positions thereof at a time at which the first medicine was disposed in the first space.

6. The medicine-dispensing apparatus according to claim 1, wherein the medicine-pushing assembly dispenses the plurality of medicines placed on the frame assembly by continuous movement thereof due to the power supply, and
wherein the plurality of medicines placed on the frame assembly are dispensed one by one by repetition of movement in the second direction for a predetermined period of time and halting for a predetermined period of time during the continuous movement of the medicine-pushing assembly.

7. The medicine-dispensing apparatus according to claim 6, wherein the medicine-pushing assembly includes a plurality of dividers for partitioning the plurality of medicines, and
wherein the plurality of dividers are moved in the second direction so as to move the plurality of medicines placed on the frame assembly in the second direction, are subsequently retracted into the internal space, and are subsequently returned to initial positions thereof after lapse of the predetermined period of time taken by the halting.

8. The medicine-dispensing apparatus according to claim 1, wherein the medicine-pushing assembly includes a plurality of dividers for partitioning the plurality of medicines,
wherein each of the plurality of dividers includes a plurality of divider parts, and
wherein a divider part that is positioned at a furthest downstream among the plurality of divider parts has a height lower than that of any of the remaining divider parts.

9. The medicine-dispensing apparatus according to claim 1, wherein the protrusion is provided at a center of the rotating assembly.

10. The medicine-dispensing apparatus according to claim 9, wherein the medicine-pushing assembly further includes a separation-prevention assembly for restricting a range of upward projection of the medicine-pushing assembly, the separation-prevention assembly including a guide hole, which is formed in a lateral side of the frame assembly so as to open downward and an engagement protrusion, which is provided on a lateral surface of the medicine-pushing assembly adjacent to the fitting groove so as to be engaged with an upper side of the guide hole.

11. The medicine-dispensing apparatus according to claim 1, wherein the frame assembly is recessed in the first direction at at least part of a surface thereof, on which the plurality of medicines are placed, so as to prevent abnormal movement of the plurality of medicines during movement of the medicines in the second direction.

* * * * *